United States Patent [19]

Chapoteau et al.

[11] Patent Number: 4,994,395
[45] Date of Patent: * Feb. 19, 1991

[54] CHROMOGENIC CRYPTAND REAGENTS AND METHODS FOR DETERMINING CATION CONCENTRATIONS IN TEST SAMPLES CONTAINING INTERFERING CATIONS

[75] Inventors: Eddy Chapoteau, Brooklyn; Bronislaw P. Czech, Peekskill; Carl R. Gebauer, Crompond; Koon-Wah Leong, Ossining; Anand Kumar, Southfields, all of N.Y.

[73] Assignee: Technicon Instruments Corporation, Tarrytown, N.Y.

[*] Notice: The portion of the term of this patent subsequent to Feb. 28, 2006 has been disclaimed.

[21] Appl. No.: 38,741

[22] Filed: Apr. 15, 1987

[51] Int. Cl.$^5$ .................. G01N 33/20; G01N 31/20; G01N 33/50; C07D 498/02
[52] U.S. Cl. ........................... 436/79; 436/74; 436/73; 436/169; 436/501; 436/170; 436/805; 540/469; 540/468
[58] Field of Search ................. 540/469, 468; 436/79, 436/501, 805, 170, 169, 73

[56] References Cited

U.S. PATENT DOCUMENTS

| | | | |
|---|---|---|---|
| 3,888,877 | 6/1975 | Lehn | 540/469 |
| 4,107,180 | 8/1978 | Dye et al. | 540/469 |
| 4,156,683 | 5/1979 | Lehn | 540/469 X |
| 4,367,072 | 1/1983 | Vogtle et al. | 436/501 |
| 4,808,539 | 2/1989 | Chapoteau et al. | 540/469 |
| 4,843,158 | 6/1989 | Smith | 540/469 |

FOREIGN PATENT DOCUMENTS 3202779 8/1983 Fed. Rep. of Germany ...... 534/752

OTHER PUBLICATIONS

Analytical Separations, p. 768.
Cram, Angew. Chem. Int. Ed. Eng., vol. 25, pp. 1039 to 1057 (1986).

*Primary Examiner*—Floyd D. Higel
*Attorney, Agent, or Firm*—Morgan & Finnegan

[57] ABSTRACT

The invention is reagents and procedures for determining an amount of cations present in a sample, the reagent comprising
(a) one or more chromogenic cryptand compounds of formula I

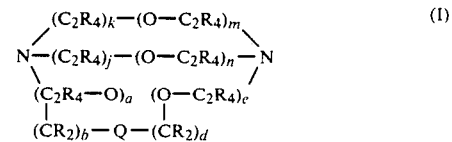

wherein
k and j, either same or different, are equal to 1 to about 5;
m and n, either same or different, are equal to 0 to about 4;
a and e, either same or different, are equal to 0 to about 2;
b and d, either same or different, are equal to 0 to about 5;
R, either same or different, is hydrogen, lower alkyl, lower alkylidene, lower alkenyl, allyl, or aryl; and —Q— is

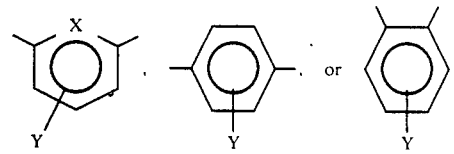

wherein
X is CH, N, or COH; and
Y includes (Abstract continued on next page.)

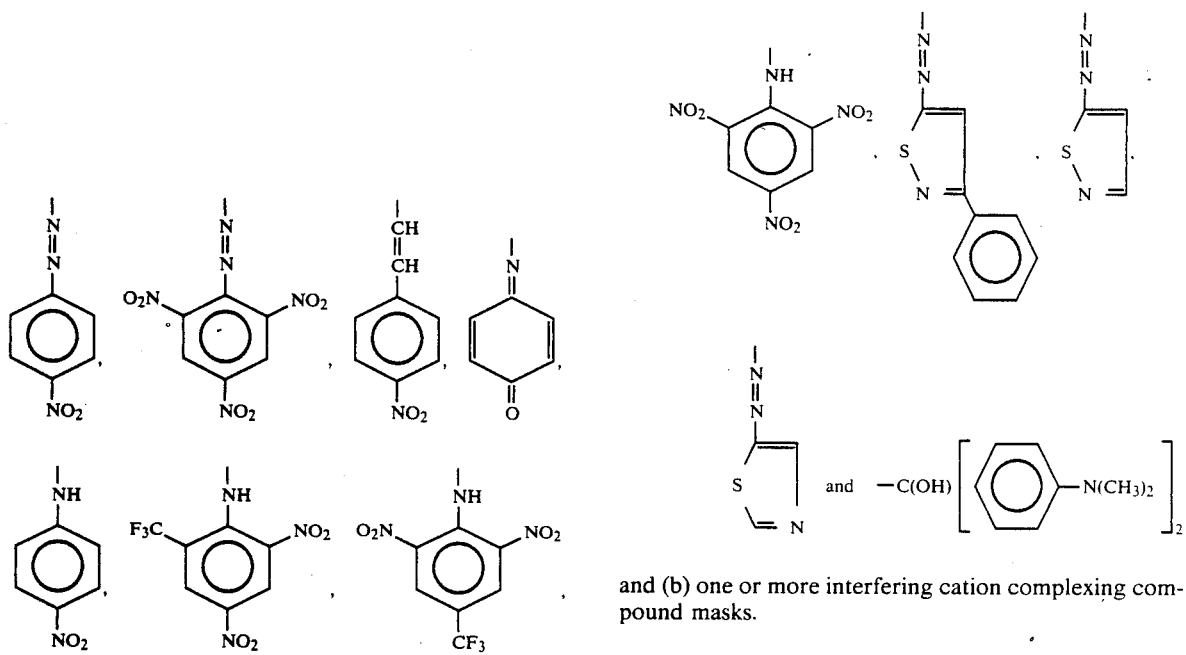
and (b) one or more interfering cation complexing compound masks.
54 Claims, 6 Drawing Sheets

CHROMOGENIC CRYPTAND REAGENTS AND METHODS FOR DETERMINING CATION CONCENTRATIONS IN TEST SAMPLES CONTAINING INTERFERING CATIONS

FIELD OF THE INVENTION

The present invention concerns a reagent for simple and rapid determination of amounts of cations, and the procedure for its use.

BACKGROUND OF THE INVENTION

The qualitative and quantitative determination of cations is of major significance in areas such as chemical and biochemical engineering for process control, in agriculture chemistry for soil research and fertilizer metering and in medicine for diagnostic and therapeutic determination of the potassium-sodium ratio. Present methods for cation determination include flame photometry and atomic absorption spectroscopy, both of which require sophisticated apparatus. Ion-sensitive cation electrodes on an ion-exchange basis generally yield sufficiently differentiated results, but are cumbersome to use.

Vogtle, U.S. Pat. No. 4,367,072 describes a process for determining ions. It is essentially based on ion-selective complexing between the ion to be determined and a complexing agent and measurement of the extinction change occurring during complexing. The complexing agent is bonded with a chromophore.

The selective complexing agent may be an oligoether, oligoester or oligoamide, containing, for example, corand, cryptand or cyclic peptide and/or polyethylene glycol groups or other hetero atom-containing groups. The covalently or heteropolarly bound chromophore is a dye or fluorescent dye or a chromogen whose absorption spectra change through interaction with non-polar ions or lipophilic molecules through charge shifts or disturbances of the mesomeric system. This principle is well known in nature and in the art. Hemin, chlorophyll and metal complex dyes and metal indicators (e.g., xylenol orange and methylthymol blue based on the colorless complexing agent ethylenediaminetetraacetic acid (EDTA)) exhibit, to a greater or lesser extent, this general configuration.

A general problem of the above-cited complexing agents is that they usually are capable of reacting only in organic media, whereas the ion being determined is, as a rule, present in an aqueous solution. Although the aqueous solutions of the ions could be transformed in many cases to organic media by concentration, inclusion in organic salts, or solvent extraction, this would not satisfy the requirements of a practical and, if necessary, automated rapid method.

Klink, et al., European Patent Publication 85,320, disclose a potassium reagent and a procedure for determining potassium ions. The reagent contains a compound of general formula

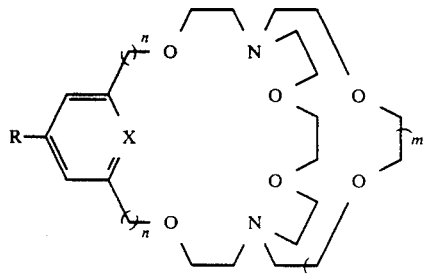

where n and m=0 or 1, X=N or COH and R=p-nitrophenylazo, 3-phenylisothiazolyl-5-azo, isothiazolyl-5-azo, thiazolyl-5-azo, 2,4,6-trinitrophenylazo, p-nitrostyryl, p-benzoquinonemonoimino and bis- (p- dimethylaminophenyl) hydroxy-methyl. The potassium ions are determined in a reaction medium consisting of water and at least one water-miscible organic solvent and in the presence of an organic base.

Klink et al. do not recognize the need for sodium ion masks in EP 85,320. They provide extinction maxima data of various cations, and state that aside from the extinction maxima for rubidium, all other extinction maxima for the various cations tested are so far removed from potassium's extinction maxima that no interference occurs. However, Klink et al. base their conclusion on data obtained from isolated cation measurements, and fail to contemplate the effect on extinction maxima for these cations in mixed cation solutions. Contrary to the conclusion reached by Klink et al., a sodium ion mask greatly enhances determination of potassium ions using chromogenic cryptands described in EP 85,320.

The present invention is directed to compounds, reagents and methods which permit rapid determination of cations in single-phase aqueous media, wherein the improvement comprises use of one or more interfering cation complexing compound masks.

SUMMARY OF THE INVENTION

Certain cryptands have high selectivity for complexing with cations and, if coupled with chromophores, yield intensive color reactions that can be evaluated analytically. Determination of cations is enhanced by using reagents of the present invention which contain one or more interfering cation complexing compound masks. For example, reagents and methods of the invention are effective for determining potassium ion concentration of a sample comprising a mixture of potassium and sodium ions. Reagents and methods of the invention are also effective for determining sodium ion concentration of a sample which comprises a large amount of sodium ions, wherein a predetermined quantity of sodium ion is screened from reacting with the chromogenic cryptand by complexing with a predetermined quantity of one or more sodium complexing compound masks. Such reagents and methods are useful in determining sodium ion concentration in undiluted samples such as serum samples drawn directly from a patient. Reagents and methods of the invention are effective for determining sodium ion concentration of a sample comprising a mixture of sodium and potassium ions. These and other advantages will be more clearly described in the detailed description of the application.

The invention relates to reagents and procedures for determining amounts of cations present in a sample, the reagent comprising one or more chromogenic cryptand compounds of formula I

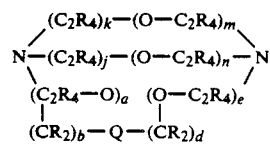

wherein
- k and j, either same or different, are equal to 1 to about 5;
- m and n, either same or different, are equal to 0 to about 4;
- a and e, either same or different, are equal 0 to about 2;
- b and d, either same or different, are equal to 0 to about 5;
- R, either same or different, is hydrogen, lower alkyl, lower alkylidene, lower alkenyl, allyl or aryl; and
—Q— is

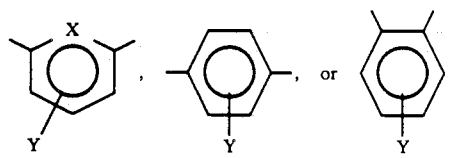

wherein
X is CH, N, or COH; and
Y includes

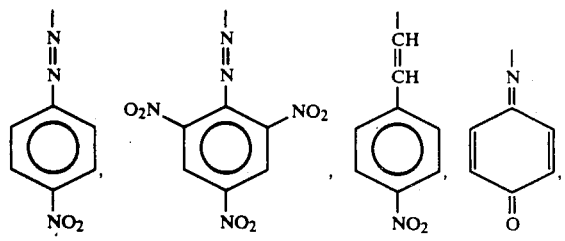

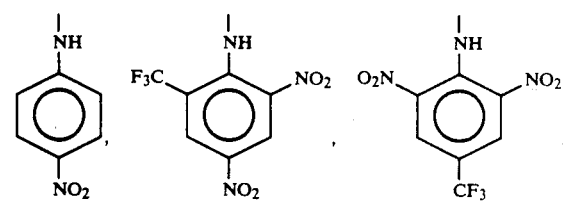

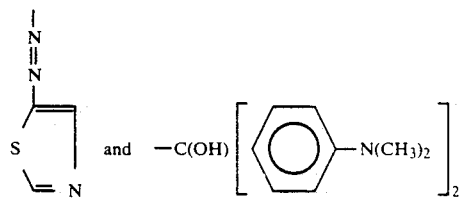

and one or more interfering cation complexing compound masks. Suitable interfering cation complexing compound masks are non-chromogenic and include spherands, hemispherands, cryptahemispherands, cryptands, and corands.

Spherands, hemispherands, and cryptahemispherands which are structurally oriented so as to complement a particular cation are preferred in the present invention. Such masks may be referred to as "pre-organized".

Cryptands and corands which have cavity sizes matching particular cation diameters are also preferred in the present invention.

When the interfering cation is sodium, suitable masks include but are not limited to

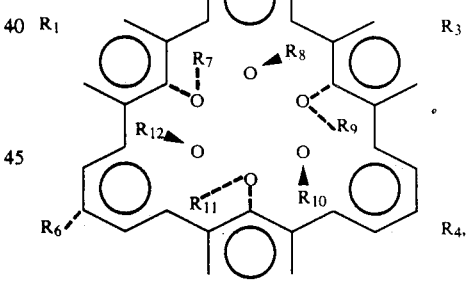

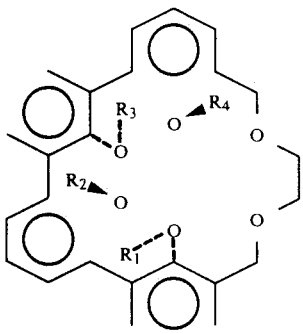

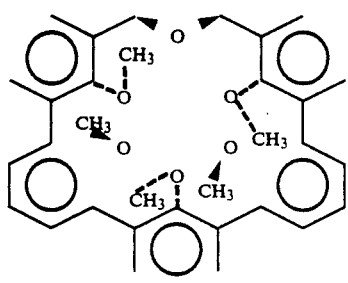

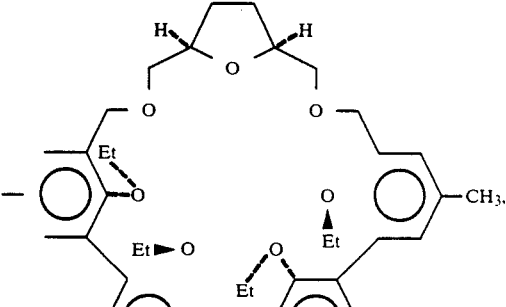

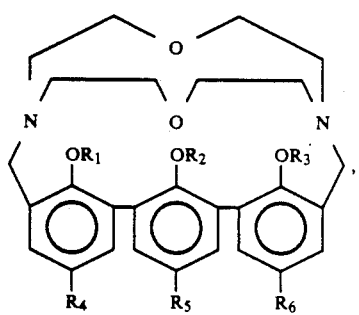

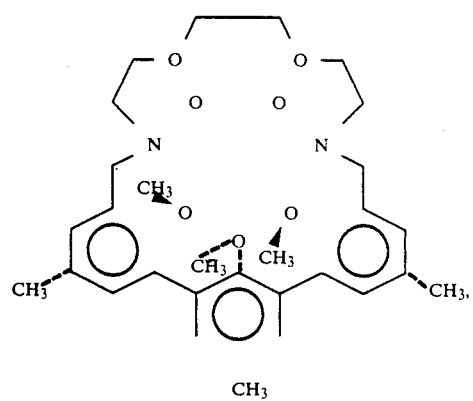

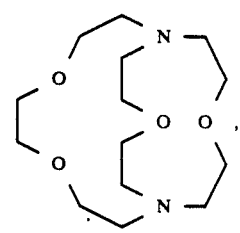

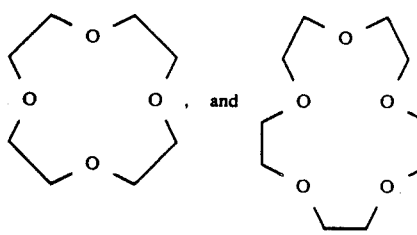

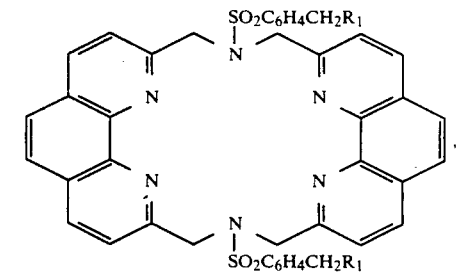

where $R_1$, $R_2$, $R_3$, $R_4$, $R_5$, $R_6$, $R_7$, $R_8$, $R_9$, $R_{10}$, $R_{11}$, and $R_{12}$, same or different, is hydrogen, lower alkyl, lower aryl, lower alkenyl, allyl or lower alkylidine. Kryptofix 2.1.1 is surprisingly effective as a sodium mask. Sodium ion complexing is beneficial in determining potassium in a sample such as blood serum which contains a high concentration of sodium. The reagent further comprises one or more water-miscible organic solvents and a buffer. The reagent may comprise a surfactant.

When the interfering ion is potassium, suitable masks include but are not limited to

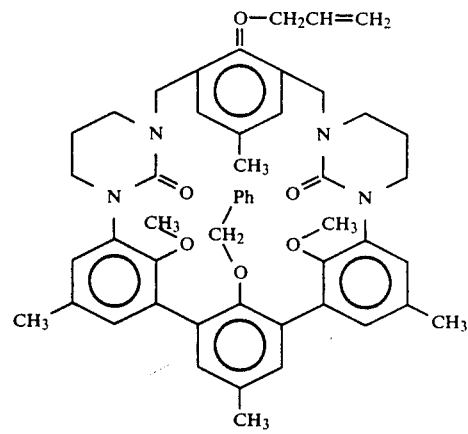

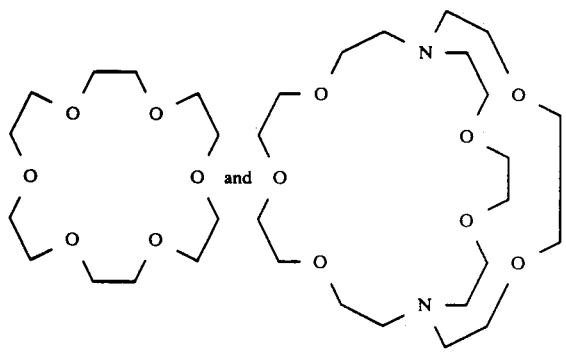

where $R_1$ is hydrogen, lower alkyl, lower aryl, lower alkenyl, allyl or lower alkylidine.

DETAILED DESCRIPTION OF THE INVENTION

Figure 1:
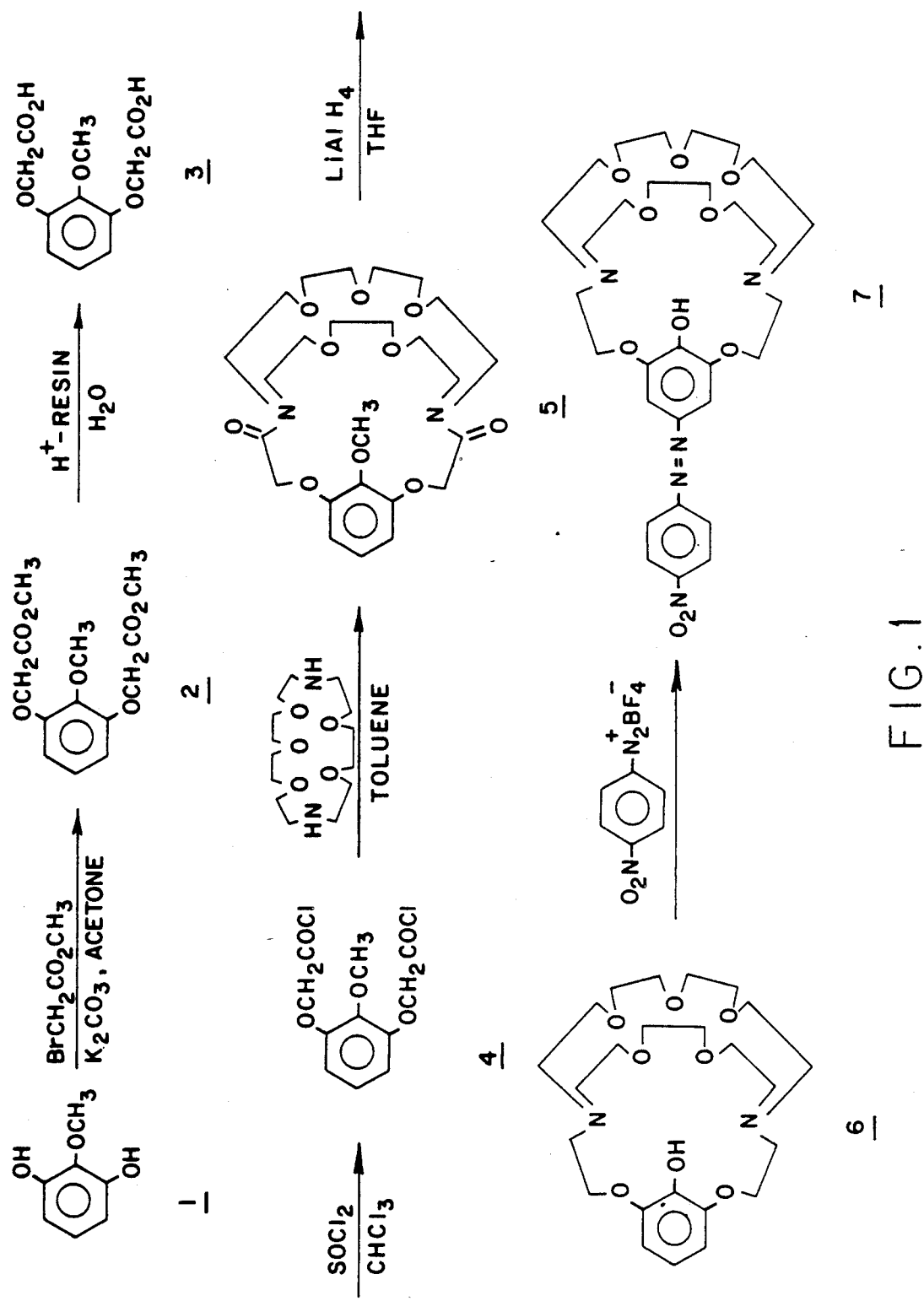
FIG. 1: Reaction pathway for synthesizing chromogenic cryptand 3.2.2.

The invention relates to reagents and methods for determining the amount of cations in a sample. The invention provides quantitative determination of cations in blood serum and other biological fluids by spectrophotometric technique in a homogeneous single phase solvent system that requires no sample pretreatment. The reagent comprises chromogenic cryptands and one or more interferinq cation complexing compound masks. Suitable interfering cation complexing compound masks are non-chromogenic and include spherands, hemispherands, cryptahemispherands, cryptands and corands.

The compounds of this invention may be utilized in compositions for making cation determinations on automated clinical chemistry analyzers such as the Technicon CHEM-1 ® clinical chemistry analyzer, the Technicon RA-1000 ® clinical chemistry analyzer and the Technicon SMAC ® clinical chemistry analyzer. Additionally, the compounds of this invention may be utilized in compositions for making cation determinations on industrial or other non-clinical chemistry automated analyzers such as the Technicon TRAACS 800 TM analyzer. Moreover, the compounds of this invention may be utilized in compositions for making cation determinations by manual methods or standard UV/vis spectrophotometers.

In one embodiment of the invention, reagents and methods of the invention are used for determining potassium ion concentration of a sample comprising a mixture of potassium and sodium ions. The sodium ion complexing compound mask prevents sodium ions from complexing with chromogenic cryptands, thereby providing favorable conditions for promoting chromogenic cryptand-potassium ion complex formation.

In another embodiment of the invention, reagents and methods of the invention are used for determining sodium ion concentration of a sample comprising a mixture of potassium and sodium ions. The potassium ion complexing compound mask prevents potassium ions from complexing with chromogenic cryptands, thereby providing favorable conditions for promoting chromogenic cryptand-sodium ion complex formation.

In another embodiment of the invention, reagents and methods of the invention are used for determining sodium ion concentration of a sample comprising high levels of sodium ions which may not be accurately detected by conventional sodium ion detection methods. A predetermined quantity of sodium ion complexing compound mask is used to prevent a predetermined quantity of sodium ions from complexing with chromogenic cryptands. Chromogenic cryptand-sodium ion complex formation is monitored to determine the remaining quantity of sodium ions, i.e., the amount of sodium ion Present greater than the predetermined quantity which complexes with the sodium ion complexing compound mask.

The sample fluids on which cation determinations can be performed using the compounds and compositions of this invention include biological, physiological, industrial, environmental and other types of liquids. Of particular interest are biological fluids such as serum, plasma, urine, cerebrospinal fluids, saliva, milk, broth and other culture media and supernatant, as well as fractions of any of them. Other sources of sample fluid which are tested by conventional methods are also contemplated as within the meaning of the term "sample" as used herein, and can have ionic determinations performed on them in accordance with this invention.

The skilled artisan will recognize that the presence of other ionic species, i.e., calcium, magnesium, and lithium, may also be determined using the compounds and compositions of this invention. The chromogenic cryptands may be used to produce color in the visible range upon interaction with cations.

The solvent system consists of water and water miscible organic solvent in proportions to obtain maximum sensitivity but to avoid sample pretreatment, such as protein precipitation, extraction or phase separation.

Cyclic ethers, glycol ethers, amides, aliphatic alcohols with, for example, three to eight carbon atoms and/or sulfoxides possess excellent photometric and visually evaluable color gradations and are suitable water-miscible organic solvents useful in the present invention.

Dioxane and tetrahydrofuran are particularly suitable as cyclic ethers, while ethylene glycol monoalkyl ethers, particularly methyl, ethyl, propyl and butyl cellosolve, are suitable as glycol ethers, and formamide, dimethylformamide (DMF), pyrrolidone and N-alkylpyrrolidones, e.g., N-methylpyrrolidone (NMP), are suitable as amides.

Aliphatic alcohols such as methanol and ethanol are also suitable, but better results are obtained in alcohols with three to eight carbon atoms such as isopropanol, n-propanol, butanols, amyl alcohols, hexanols, heptanols and octanols.

Dimethyl sulfoxide is also a suitable solvent. The water-dioxane solvent system has proved particularly advantageous.

It has been found that a large number of water-miscible organic solvents, such as, for example, acetone, methyl ethyl ketone and glacial acetic acid are unsuitable as reaction media.

The solvent system of the present invention differs from Klink, et al., which teaches suitable reagent solvent systems as including a water-miscible organic solvent in amounts achieving a water to organic solvent ratio of about 1:4 to 1:6.

The present invention teaches solvent systems of about 1:0.5 to 1:2, and preferably includes a surfactant and higher pH. The solvent system of the present invention obviates the need for removal of protein from a serum sample.

Other components may also be included in the compositions of this invention, such as buffers and stabilizers. Additional ion masks may be employed to remove the effect of interfering ionic species.

Because of the importance of maintaining pH at a specific level in making accurate cation determinations, buffer may be included in compositions of this invention for the purpose of controlling the pH. Suitable buffers for maintaining the pH include cyclohexylaminopropanesulfonic acid (CAPS), cyclohexylaminoethanesulfonic acid (CHES), triethanolamine, diethanolamine, ethanolamine, 2-naphthalene sulfonic acid, and salicylic acid. Preferably, in making a cation determination, the pH of the composition is maintained at about 9-12.

The compositions of this invention may also include a surfactant in order to aid in protein solubilization. Surfactants are also used in many automated analyzers for hydraulic reasons. Suitable surfactants for use in the compositions of this invention include sorbitan monooleate (commercially available as Tween-80® from ICI Americas Co. of Wilmington, Del.) and polyoxyethylene lauryl ether (commercially available as Brij-35® from ICI Americas of Wilmington, Del.).

Reagents of the invention are mixed with a sample to be tested. After mixing of reagent and sample, absorbance of the resulting solution is measured to determine concentration of the cation of interest.

The invention also includes reagents and methods for determining cations in a sample, wherein said method employs a reagent comprising a chromogenic cryptand, an interfering cation complexing compound mask, and a carrier matrix comprising a porous or wettable material. In a single layer format, the carrier matrix can be formed from materials such as paper, cardboard, porous polymers, polymer fiber and natural felts, and other suitable materials. Preferred as carrier matrix materials are filter paper, and porous high density polyethylene. In a multilayer analytical element format, the buffer can be stored in an upper layer and the cryptand in a lower layer in a superposed laminar fashion. The matrices for these layers can be formed from materials such as gelatin, water soluble or water swellable polymers, and other suitable materials. In addition to those two layers, a spreading layer, a reflecting layer and a support material can be incorporated to form an integral analytical element.

In a preferred embodiment of the invention, the sample is blood serum or plasma, the carrier matrix is a device that is a dimensionally stable, uniformly porous, diffusely reflective single layer formed of a polymeric non-fibrous matrix, and the method comprises the following steps:

(a) preparing a reagent mixture consisting essentially of one or more water-soluble polymeric binders, a surfactant, a chromogenic cryptand according to formula I, an interfering cation complexing compound mask, water and a buffer;

(b) adding the reagent mixture to the device;
(c) evaporating the water of the reagent mixture;
(d) adding the sample to the device; and
(e) measuring reflectance of the device.

Preferred reagents comprise one or more water soluble polymeric binders selected from the group including polyvinyl alcohol, polyvinyl pyrrolidone, polyacrylic acid, methyl cellulose, hydroxymethylcellulose and gelatin.

Preferred reagents further comprise one or more organic buffers. Examples of suitable organic buffers include triethanolamine, diethanolamine, ethanolamine, 2-naphthalene sulfonic acid, CAPS and CHES. Suitable buffers maintain a pH in the range of about 9 to about 12.

The matrix may be constructed in one of several ways. One suitable way involves sintering fine particulates of a high-density polyethylene, ultra-high molecular weight polyethylene, polypropylene, polyvinylidene fluoride, polytetrafluoroethylene, nylon, polyvinylchloride, polyesters, polysulfones and blends thereof. The matrix may be coated with a hydrophilic surfactant selected from the group including polyoxyethyleneoctyl phenols, polyoxyethylenenonyl phenols, and polyoxyethylenelauryl ethers. By incorporating a suitable carrier matrix with the reagent, cation determination can be done using such a device.

Such a device lends itself to dry storage when not in use, thus enabling long shelf-life, and can be pressed into service immediately simply by contacting it with a small portion of the test sample, be it blood, serum, urine or other aqueous solution to be assayed. It can take on such formats as a dip-and-read strip for urine or a test slide for use with an automatic blood analyzer, or can form a multilayer structure such as is described in U.S. Pat. Nos. 3,992,158 and 4,292,272.

It is desirable that the carrier matrix comprise a porous or wettable material. Thus, in a single layer format the carrier matrix can be formed from materials such as paper, cardboard, porous polymers, polymer fiber and natural felts, and other suitable materials. Especially preferred as carrier matrix materials are filter paper, and porous high density polyethylene. In a multilayer analytical element format, the buffer can be stored in an upper layer and the chromogenic cryptand in a lower layer in a superposed laminar fashion. The matrices for these layers can be formed from materials such as gelatin, water soluble or water swellable polymers, and other suitable materials. In addition to these two layers, a spreading layer, a reflecting layer and a support material can be incorporated to form an integral analytical element.

The device is prepared by incorporating the carrier matrix with the test composition and, if desired, providing dried matrix with a support.

Thus the composition is applied to the matrix by innoculating the surface of the matrix or by dipping it into a solution of the composition. The thus-impregnated matrix can then be dried at room temperature or at elevated temperatures provided the temperature is not so high as to deleteriously affect the composition.

The dried, impregnated carrier matrix can then be mounted, if desired, on a suitable support such as a circumferential frame which leaves the matrix exposed to the middle; or the matrix can be mounted at one end of a plastic strip, the other end serving as a convenient handle.

In one embodiment of the invention, the test sample containing sodium is contacted with the surface of the test device and the detectable response is measured at 650 nm or other appropriate wavelength on a reflectometer. Experiments using varied known sodium concentrations yield a dose/response curve enabling clear correlation between changes in percent reflectance and sodium concentration in the millimollar range.

The following examples illustrate but are not intended to limit the scope of the present invention.

EXAMPLES

EXAMPLE 1

A preferred chromogenic 3.2.2 cryptand was synthesized by the reaction pathway shown FIG. 1, and is shown as compound 7.

Bis(1,3-methylacetoxy)-2-methoxybenzene 2

To a stirred mixture of anhydrous $K_2CO_3$ (30 g) and methyl bromoacetate (30.5 g, 0.20 mol) in 400 ml of acetone was added dropwise under nitrogen a solution of 2-methoxyresorcinol 1 in 100 ml of acetone. The mixture was refluxed for 30 h. Filtration of the inorganic material and evaporation of the solvent gave a residue which was column chromatographed on silica gel with methylene chloride - methanol (50:1) to afford 19.3 g (95%) of 2 as a colorless, viscous liquid which solidified during storage in the form of white crystals; M.P. 70°-72° C. Calcd. for $C_{13}H_{16}O_7$ (percent): C, 54.33; H, 5.67 Found: (percent): C, 54.82; H, 5.55.

1,3-Di(oxyacetic acid)-2-methoxybenzene 3

Dimethylester 2 (4.00 g, 14 mmol) was suspended in 250 ml of water containing Amberlyst IR-120(H+)(0.5 g). The mixture was refluxed for 8 h. The resin was filtered and the water solution concentrated. A white cyrstalline material was separated and dried to give 3.33 g (93%) of diacid 3; M.P. 148°-150° C. (lit.[1] mp 150°-152° C.).

Diacid Chloride 4

Diacid 3 (2.50 g. 9.8 mmol) was suspended in 15 ml of chloroform and the mixture was heated to reflux. Thionyl chloride (3 ml) was added dropwise to the refluxing suspension and it was refluxed overnight to give an almost clear solution. The reaction mixture was cooled, filtered, and evaporated in vacuo to afford 2.74 g (96%) of a pale yellow purification.

Methoxybenzo Cryptand Diamide 5

Solutions of diacid chloride 4 (1.99 g, 6.81 mmol) in 100 ml of toluene and Kryptofix ® 3.2 (2.08 g, 6.81 mmol) and triethylamine (1.77 g) in 100 ml of toluene were simultaneously added to 250 ml of rapidly-stirred toluene at 0° C. under nitrogen with two syringe pumps during 4 h. After completion of the addition, the reaction solution was stirred at room temperature overnight. The solid material was filtered and the filtrate was evaporated in vacuo. The residue was chromatographed on silica gel with chloroform-ethanol (20:1) as eluent to give 2.38 g (54%) of 5 as a colorless, hygroscopic oil. Calcd. for $C_{25}H_{38}N_2O_{10}$ (percent): C, 57.02; H, 7 27. Found (Percent): C, 56.80; H, 7.42.

Cryptand Phenol 6

The cryptand diamide 5 (1.25 g, 2.4 mmol) was added to a suspension of lithium aluminum hydride (0.76 g, 20.0 mmol) in tetrahydrofuran (80 ml) and the mixture was refluxed for 20 h. After cooling, 4.0 ml of 5% NaOH was added. The inorganic material was filtered and washed several times with hot tetrahydrofuran. The combined filtrate and washings were evaporated in vacuo and the residue was chromatographed on alumina to give 0.99 g (85%) of 6 as a colorless, hygroscopic oil. Calcd. for $C_{24}H_{40}N_2O_8H_2O$ (percent): C, 57.35; H, 8.42. Found (percent):C, 57.70; H, 8.32.

Chromogenic Cryptand 7

To cryptand phenol 6 (0.85 g, 1.75 mmol) was added 32% NaOH until the aqueous solution was basic. The clear, brown oil was separated and dried in vacuo. Acetic acid (20 ml) was added to the residue to give a clear solution which was cooled to 0° C. A solution of p-nitrobenzenediazonium tetrafluoroborate (0.47 g, 2.0 mmol) in water (25 ml) was added dropwise with vigorous stirring. The mixture was stirred overnight at room temperature and then evaporated to dryness. Column chromatography on alumina with chloroform-ethanol (20:1) gave 0.75 g (70%) of 7 as a dark-red oil. Calcd. for $C_{30}H_{43}N_5O_9H_2O$ (percent): C, 56.68; H, 7.13. Found (percent) C, 56.45; H, 7.18.

EXAMPLE 2

An experiment was performed to ascertain the response of the chromogenic agent of Klink et al., European Patent application number 83,320 to potassium in the presence of sodium as would be encountered in human serum samples.

Preparation of reagent was as described by Klink, et al. and when combined with aqueous sample containing zero to ten parts per million (ppm) potassium (1.5 mM) and zero or 6 mM sodium (140 ppm) gave a solution with the final concentration of individual components:

| | |
|---|---|
| 1,4-dioxane | 80% |
| morpholine | 2.4% |
| DMSO | 1.6% |
| chromogenic cryptand 2.2.2 (Klink et al.) | 0.0008% |
| aqueous sample | 16% |

When no sodium is present in sample there is a significant response to potassium as described by Klink et al. However, in the presence of even low concentrations of sodium as studies here, the response to potassium is negligible. It is clear that such a chromogenic reagent, by itself, has insufficient selectivity to determine the concentration of potassium ion in human serum or other samples where there exists a large excess of interfering sodium ions.

| K Concentration in the sample | Response, 570 nm Abs. Sample - Abs. blank |
|---|---|
| 0 ppm | 0.0404 |
| 2 ppm | 0.1058 |
| 4 ppm | 0.1459 |
| 6 ppm | 0.1697 |
| 8 ppm | 0.1853 |
| 10 ppm | 0.1978 |
| | Response, 570 nm |

-continued

| K concentration | Na concentration | Abs. Sample-Abs. blank |
|---|---|---|
| 0 ppm | 6 mM | 0.0915 |
| 2 ppm | 6 mM | 0.0893 |
| 4 ppm | 6 mM | 0.0917 |
| 6 ppm | 6 mM | 0.0916 |
| 8 ppm | 6 mM | 0.0949 |
| 10 ppm | 6 mM | 0.0936 |

In an experiment under similar conditions to those described by Klink, et al., the response of chromogenic cryptand to potassium was studied. When sodium ion was present in the same sample, loss of chromogenic cryptand response to potassium was observed.

Reagent Formulation

A. Dissolve approximately 4.16 mg Klink et al. cryptand 2.2.2 into 5 ml 1,4-dioxane.

B. Add 2.4 ml morpholine, 1.6 ml dimethylsulfoxide and 16 ml distilled water to 80 ml 1,4-dioxane and mix.

C. Pipet 0.5 ml of solution A into 19.5 ml solution B. This solution will be used for the assay of potassium ions.

Standards

Prepare 0–10 mM NaCl in a 10 mM KCl background.

Assay

Add 0.15 ml standards to 2.1 ml of solution C and read the change in absorbance at 566 nm in a spectrophotometer.

Results

Response to potassium in absence or presence of sodium ion is shown below.

| Sample Na Concentration | Response to 10 mM Potassium |
|---|---|
| 0 mM | 0.326 |
| 2 mM | 0.116 |
| 4 mM | 0.029 |
| 6 mM | −0.023 |
| 8 mM | −0.044 |
| 10 mM | −0.070 |

The results clearly indicate that under mixed ion conditions, the response to potassium is drastically reduced in the presence of sodium.

EXAMPLE 3

A potassium assay was performed in serum using compositions of this invention and comprising chromogenic cryptand 2.2.2. of Klink et al. (shown as formula II) below:

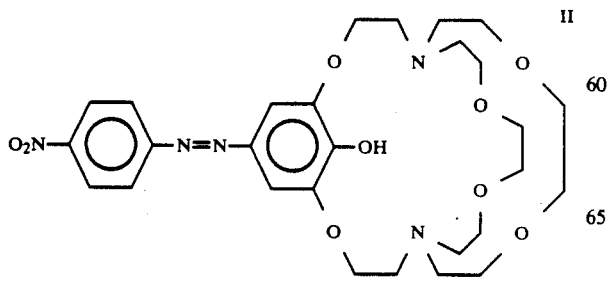

REAGENT FORMULATIONS 4.12 mg of the chromogenic compound II was dissolved into 50 ml dioxane to form a chromogenic compound - dioxane solution.

8.85 g cyclohexylaminopropanesulfonic acid was dissolved into 30 ml $H_2O$. 0.186 g ethylenediaminetetraacetic acid and 10 ml 1M tetramethylammonium hydroxide were added, and stirring was continued until all solids were dissolved. After all solids were dissolved, 5 g Tween-80 ® (ICI) were added. pH was adjusted to 12.0 using 1M tetramethylammonium hydroxide and volume was brought to 50 ml with distilled water. Finally, the chromogenic compound-dioxane solution was added, and stirring was continued until the reagent was well mixed.

Formulation (b)

A second formulation was prepared as described above except that 0.432 g Kryptofix ® 2.1.1 (E. Merck-)(a non-chromogenic sodium mask) was added.

Assay 0.98 ml reagent was mixed with 0.02 ml sample. Absorbance at 530 nm on a Beckman DU8 Spectrophotometer was measured.

A series of standard potassium samples with concentration ranging between 0 and 10 mM was prepared in a 140 mM sodium chloride solution and assayed by using formulations (a) and (b).

Results

Figure 2:
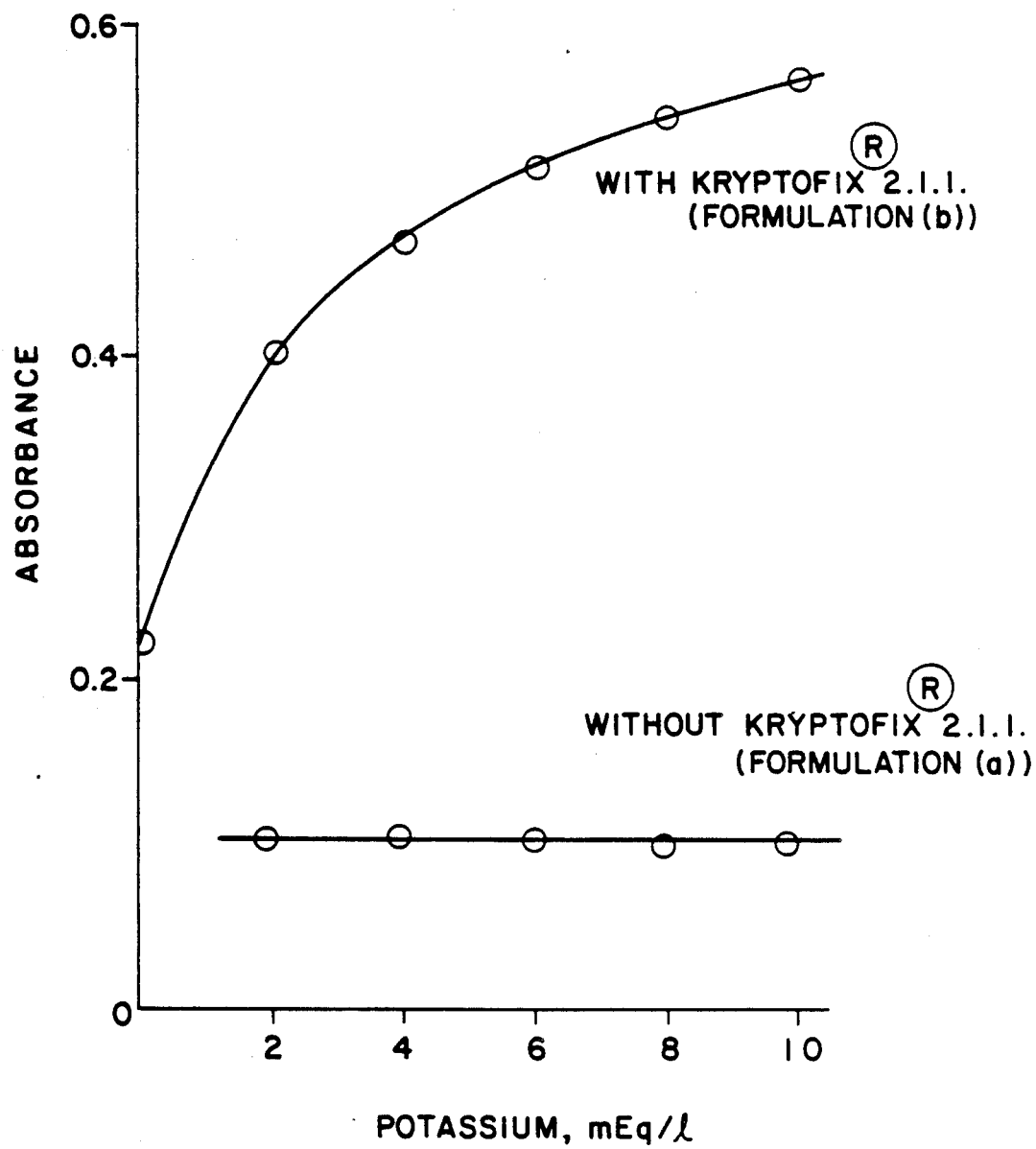
FIG. 2: Absorbance data for potassium assay with and without Kryptofix ® 2.1.1 mask.

The data for the assay of these samples with formulations (a) and (b) is represented in FIG. 2. The results clearly showed that there is no response to increasing potassium concentration in formulation (a) that contains no sodium mask Kryptofix ® 2.1.1, whereas the converse is true for the assay using formulation (b) containing Kryptofix ® 2.1.1.

EXAMPLE 4

An experiment was conducted to compare a preferred composition of the present invention with a state-of-the-art method for measuring potassium in serum.

A series of random serum samples containing a broad range of potassium concentration was obtained. The samples were assayed on a RA-1000 ® analyzer (Technicon Instruments Corporation) using the reagent formulation listed below:

| 1.69 × $10^{-4}$M | chromogenic cryptand 3.2.2 (compound 7 of FIG. 1) |
|---|---|
| 3.0 × $10^{-2}$M | Kryptofix ® 2.1.1 |
| 4.0 × $10^{-3}$M | EDTA (divalent ion mask) |
| 60% (v/v) | Ethoxyethoxyethanol (water miscible organic solvent) |
| pH 11 | CAPS 0.12M (buffer) |
| 2.5% (w/v) | Tween-80 ® (surfactant) |

The parameters on the RA-1000 ® instrument were as follows:

| sensitivity | 12.0 mA/mM |
|---|---|
| method | end point |
| temperature | 37° c. |
| wavelength | 540 nm |
| sample volume | 4 µl |
| reagent volume | 395 µl |

| | |
|---|---|
| delay | 5 min. |
| pH | 11.5 |
| dilution ratio | 1:100 |

Result

The absorbance output from the RA-1000 ® instrument for each sample was recorded and converted to potassium concentration. The same set of serum samples was also assayed by RA-1000 ISE ® module for potassium concentrations.

| Correlation data on RA-1000 ® analyzer Reference method RA-1000 ISE ® | |
|---|---|
| slope | 1.10 |
| intercept | −0.26 |
| correlation coefficient | 0.9704 |
| number of serum samples | 41 |
| Linear range, mM | 0–14 |
| Precision, CV | 2.2% |

The data show good agreement between the method of the present invention and the state-of-the-art ISE methodology.

EXAMPLE 5

A sodium assay was performed in serum using compositions of this invention comprising a controlled amount of non-chromogenic sodium mask Kryptofix ® 2.2.1 and chromogenic cryptand 2.2.2. of Klink et al. (structure II)

Reagent Formulation 6.63 g cyclohexylaminopropanesulfonic acid was dissolved into 80 ml H$_2$O. 0.186 g ethylenediaminetetraacetic acid and 10 ml 1M tetramethylammonium hydroxide were added. Stirring continued until all solids were dissolved and then 80 mg Kryptofix ® 2.2.1 and 0.2 g Triton ® x-100 were added. pH was adjusted to 11.15 with 1M tetramethylammonium hydroxide. 2.5 ml solution of the chromogenic cryptand 2.2.2 (2.1 mg in 2.5 ml dioxane) was then added and volume was increased to 100 ml with distilled water.

Assay 0.98 ml reagent was mixed with 0.02 ml sample, and absorbance at 600 nm with a Beckman DU8 Spectrophotometer was measured. A series of standard samples with known sodium concentration was assayed.

Result

Figure 3:
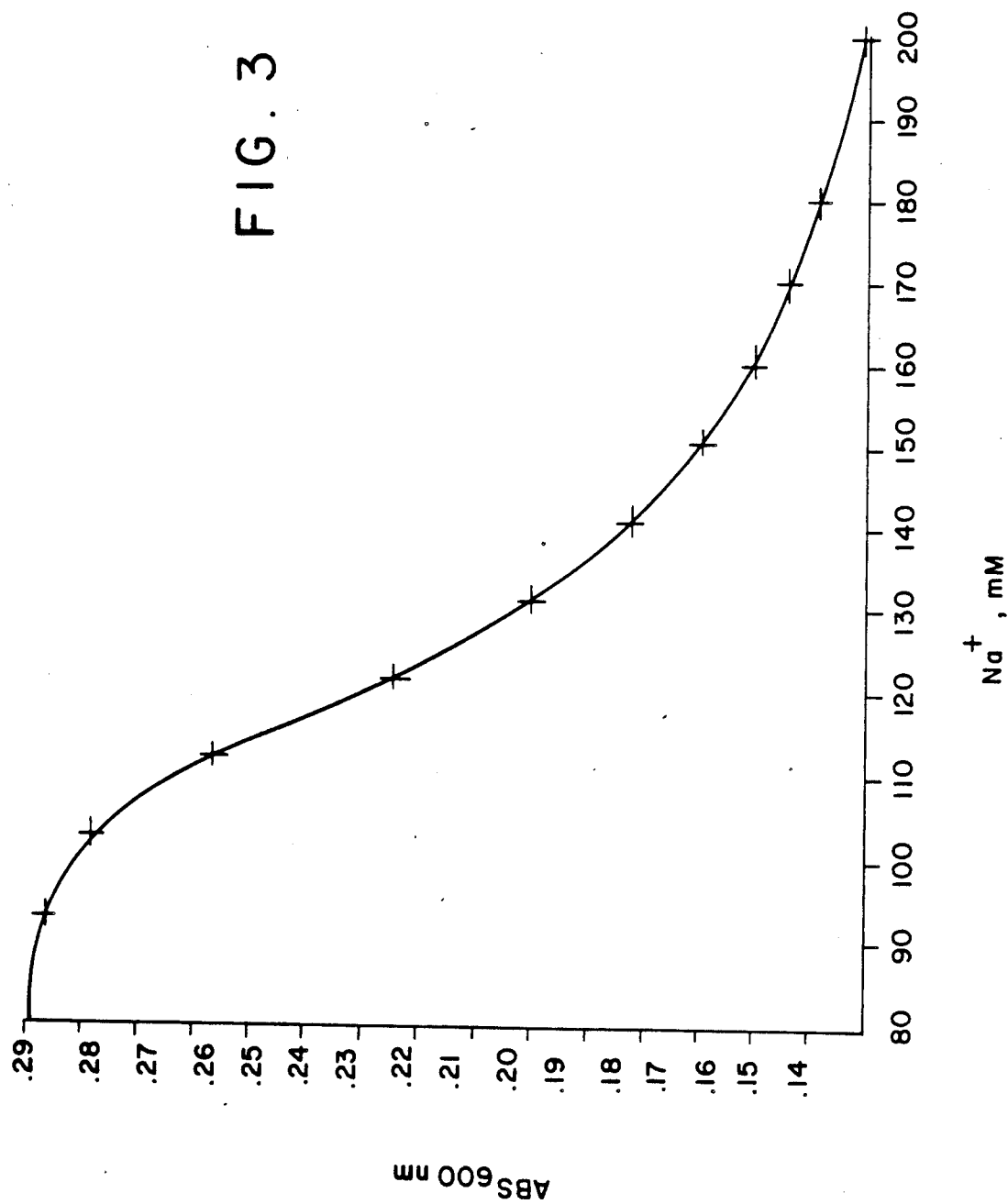
FIG. 3: Absorbance data for sodium assay with Kryptofix ® 2.2.1 mask.

The plot of sodium concentration against absorbance measured at 600 mm is shown in FIG. 3.

EXAMPLE 6

An experiment was conducted to compare a preferred composition of the present invention with a state-of-the art method for measuring sodium in serum.

A series of random serum samples containing a broad range of sodium concentration was obtained. The samples were assayed on RA-1000 ® instrument using the reagent formulation of Example 5. The parameters on the RA-1000 ® instrument were set as follows:

| | |
|---|---|
| Sample Volume | 5.0 µl |
| Reagent Volume | 395 µl |
| Optical Filter | 600 nm |
| Temperature | 37° C. |
| Delay | 5 min. |
| Assay type | end point |

The absorbance output from the RA-1000 ® instrument for each sample was recorded and converted to sodium concentrations using the plot of a calibration curve. The same set of serum samples were also assayed by RA-1000 1SE ® module for sodium concentrations.

Figure 4:
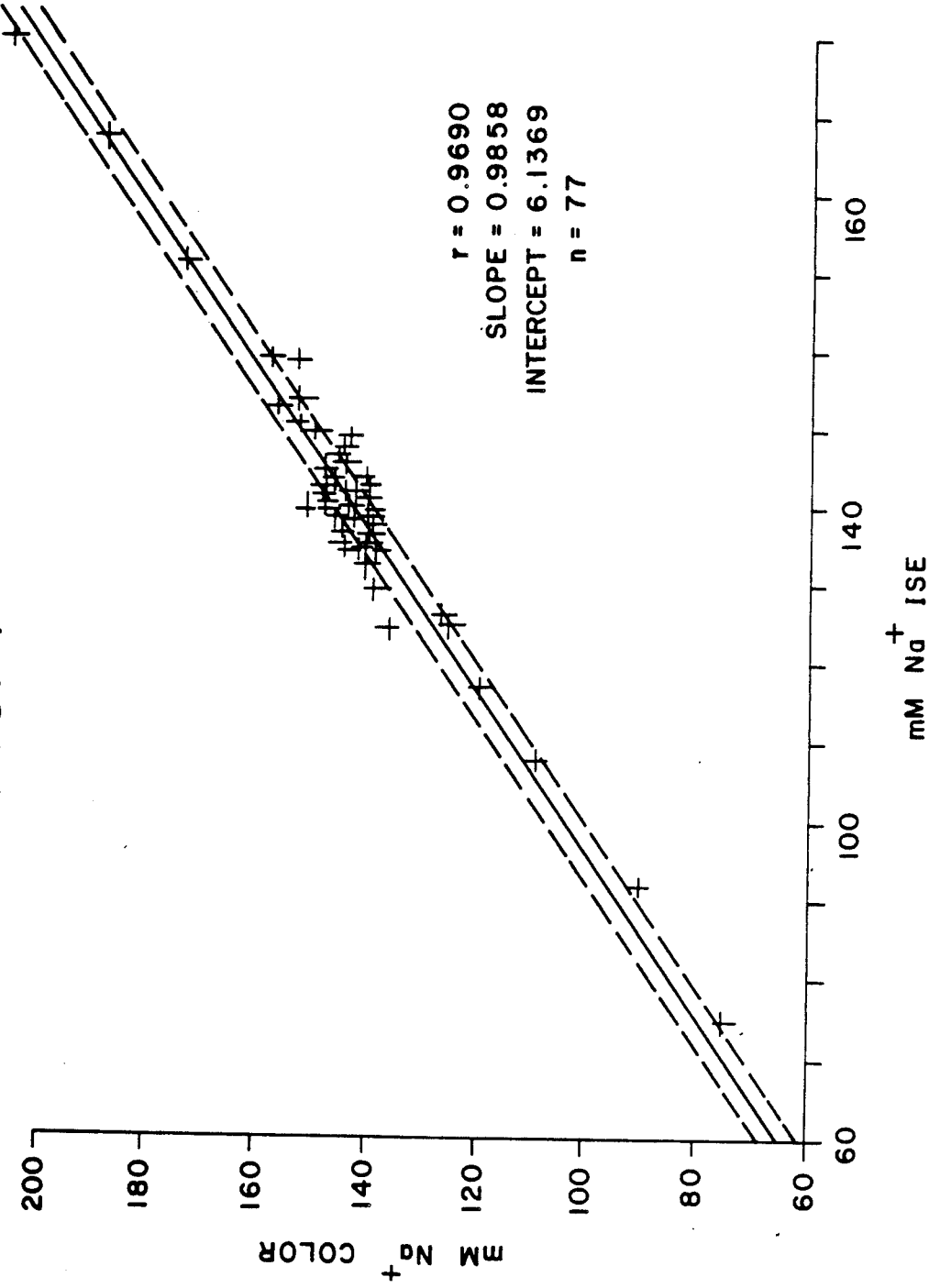
FIG. 4: Correlation plot of sodium assay with Kryptofix ® 2.2.1 mask and state-of-the-art method.

The assay results of the present invention were plotted against the assay results of the state-of-the-art RA-1000 ISE ® module. The plot is depicted in FIG. 4 and clearly shows a good correlation between the present invention and the state-of-the-art methodology.

EXAMPLE 7

An experiment was conducted to compare a second preferred composition of the present invention with a state-of-the-art method for measuring sodium in serum.

A series of random serum samples containing a broad range of potassium concentration was obtained. The samples were assayed on RA-1000 ® instrument (Technicon Instruments Corporation) using the reagent formulation listed below:

| | |
|---|---|
| 1.35 × 10$^{-4}$M | Chromogenic cryptand 3.2.2. (compound 7 of FIG. 1) |
| 2.0 × 10$^{-3}$M | Cryptand 3.2.2. (potassium mask) |
| 5.0 × 10$^{-3}$M | EDTA |
| 50% (v/v) | Ethoxyethoxyethanol (water miscible organic solvent) |
| pH 11.2 | CAPS 0.15M |
| 2.5% (w/v) | Tween-80 ® |

Cryptand 3.2.2 is represented by

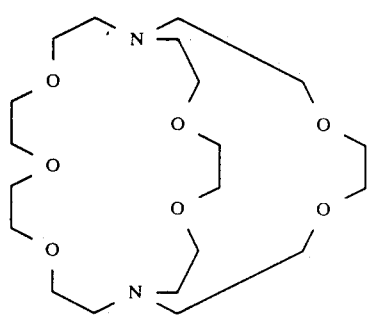

III

The parameters on the RA-1000 ® instruments were as follows:

| | |
|---|---|
| sensitivity | 1.7 mA/mM |
| method | end point |
| temperature | 37° C. |
| wavelength | 600 nm |
| sample volume | 4 µl |
| reagent volume | 395 µl |
| delay | 5 min. |
| pH | 11.2 |
| dilution ratio | 1:100 |

Result

The absorbance output from the RA-1000® instrument for each sample was recorded and converted to sodium concentrations. The same set of serum samples was also assayed by RA-1000 ISE® module for sodium concentrations.

| Correlation data on RA-1000 ® instrument Reference method RA-1000 ISE ® | |
| --- | --- |
| slope | 1.13 |
| intercept | −12.47 |
| correlation coefficient | 0.9505 |
| number of serum samples | 80 |
| Linear range mM | 80–200 |
| Precision, CV | 2.1% |

The data show good correlation between the method of the present invention and the state-of-the-art methodology.

EXAMPLE 8

The following example demonstrates the use of chromogenic cryptand 2.2.2 of Klink et al. in conjunction with Kryptofix® 2.2.1 to mask a fixed amount of sodium ions in an analytical sample allowing measurement without dilution. Dry reagent analytical element was prepared as follows.

To each ½ inch diameter porous disk (HDPE, 35 um, 1/32-inch thick), 35 microliter of a reagent mixture containing 1.0 ml distilled water, 1 mg chromogenic cryptand 2.2.2, 70 mg cryptand 2.2.1, 10 mg polyvinyl alcohol, 10 mg polyvinyl pyrrolidone, and 0.1 gm Triton®x-100 were deposited, and the disks were allowed to dry at room temperature for five hours before storing in a desiccator for two hours.

The disks were tested with 25 microliter analytical sample containing 0.2M CAPS buffer, pH 11.0. The diffuse reflective signals after two minutes incubation at room temperature were measured at 650 nm on a modified Infra-Alyzer (Technicon Instruments Corporation). The reflectance, R measurements were transformed to K/S functions where $$K/S = \frac{(1 - R)^2}{2R}.$$

Figure 5:
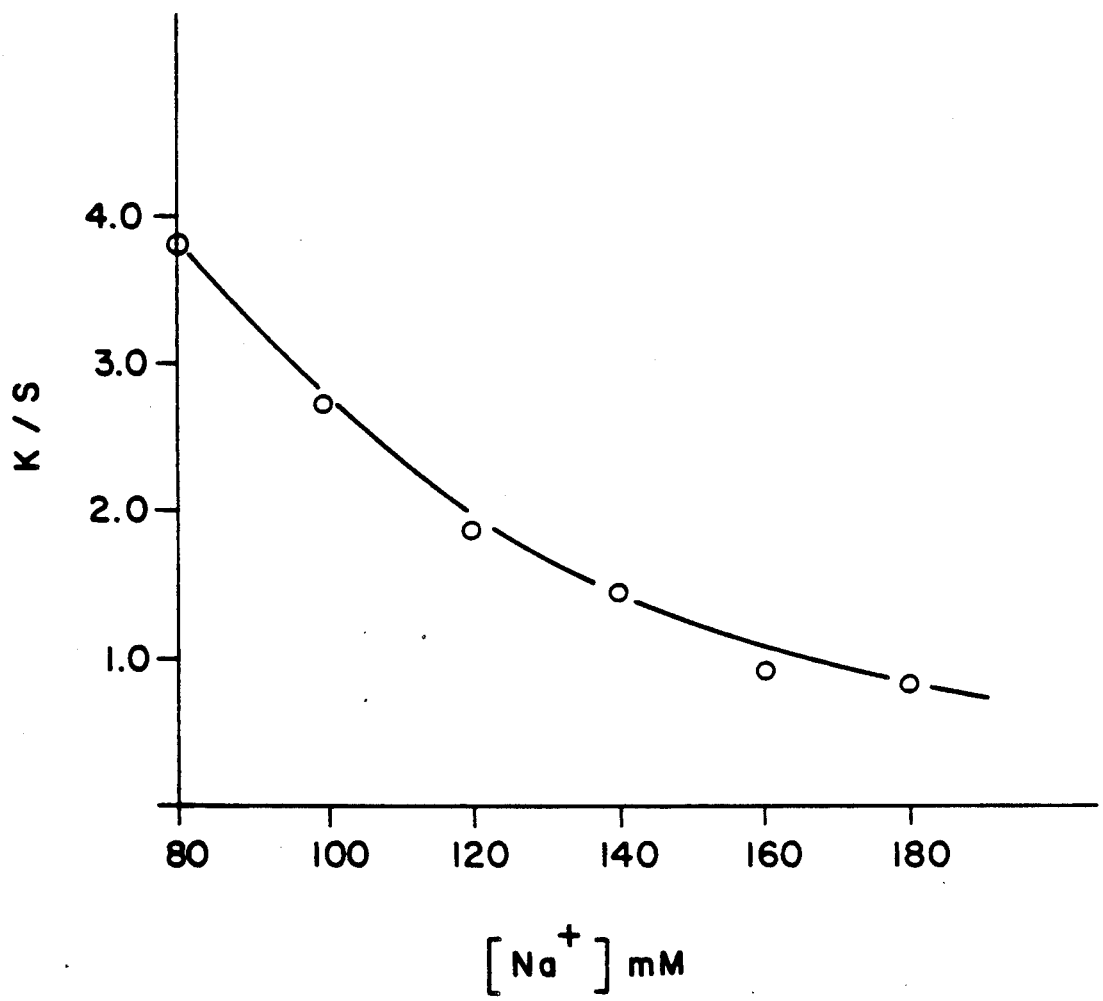
FIG. 5: Dry chemistry analytical element sodium response to chromogenic cryptand 2.2.2 with Kryptofix ® 2.2.1 mask.
Figure 6:
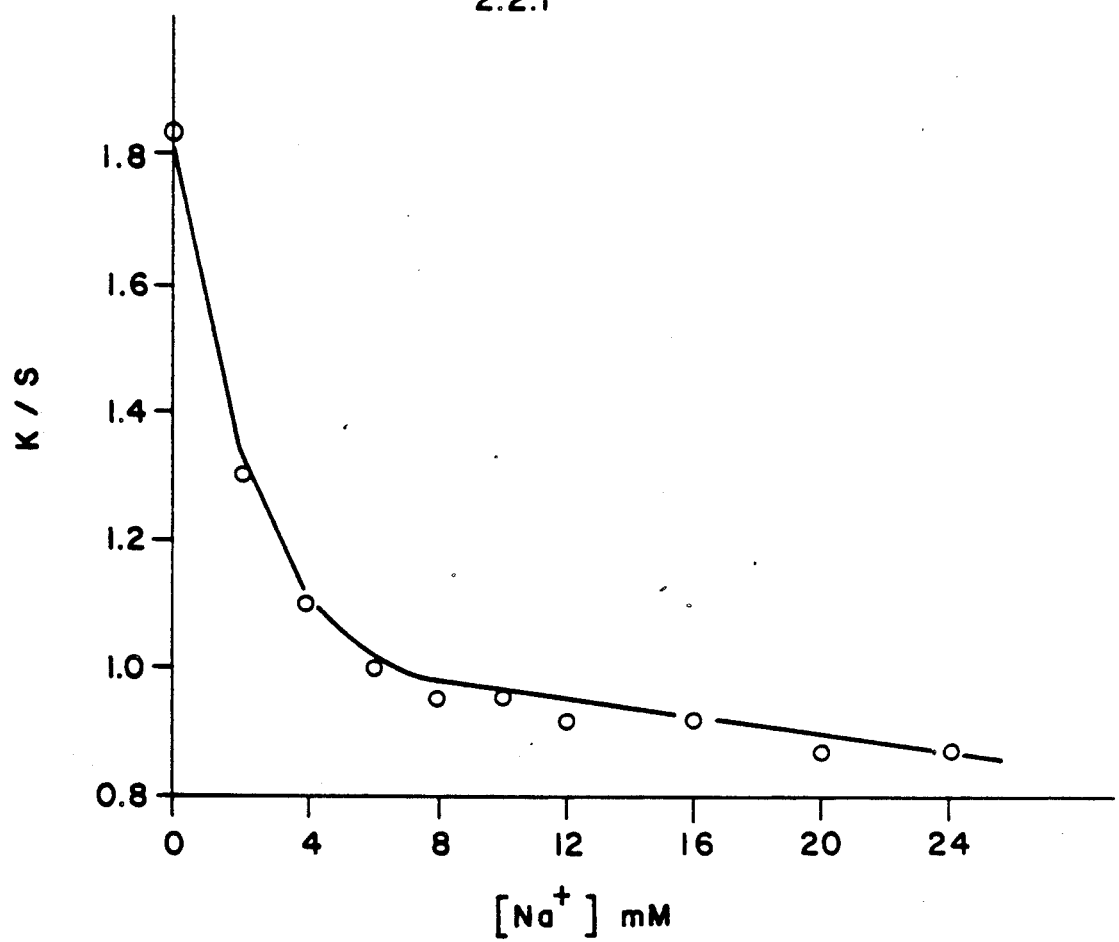
FIG. 6: Dry chemistry analytical element sodium response to chromogenic cryptand 2.2.2. without Kryptofix ® 2 2.1 mask.

The plot of K/S versus sodium concentration as shown in FIG. 5 demonstrates an inverse relationship from 80 mM to 180 mM sodium. In the absence of Kryptofix® 2.2.1, the dynamic range was narrow, from zero to 20 mM sodium as shown in FIG. 6.

What is claimed is:

1. A reagent for determining the concentration of potassium cations in a sample containing potassium and interfering sodium cations, the reagent consisting essentially of:
   (a) at least one chromogenic crptand compound having the formula

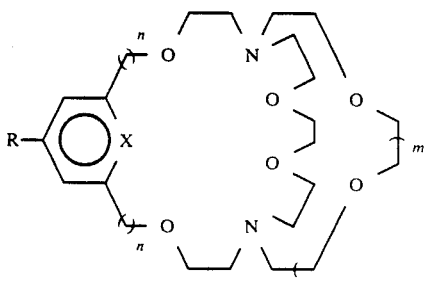

where n and m=0 or 1, X=N or COH, and R=p-nitrophenylazo, 3-phenylisothiazolyl-5-azo, isothiazolyl-5-azo, thiazolyl-5-azo, 2,4,6-trinitrophenylazo, p-nitrostyryl, p-benzoquinonemonoimino, and bis-(p-dimethylaminophenyl)hydroxymethyl, and
   (b) at least one sodium mask which reacts selectively with the interfering sodium cations.

2. A reagent according to claim 1, wherein the mask is a spherand pre-organized for the ionic diameter of sodium.

3. A reagent according to claim 2, wherein the mask is a hemispherand pre-organized for the ionic diameter of sodium.

4. A reagent according to claim 1, wherein the mask is a cryptahemispherand pre-organized for the ionic diameter of sodium.

5. A reagent according to claim 1, wherein the mask is a cryptand having a cavity size about the size of a sodium ion.

6. A reagent according to claim 1, wherein the mask is a corand having a cavity size about the size of a sodium ion.

7. A reagent according to claim 1, further comprising:
   (c) water;
   (d) a water miscible organic solvent; and
   (e) a buffer for maintaining said reagent pH at between about 9 and about 12.

8. A reagent according to claim 7, further comprising:
   (f) a surfactant; wherein the water to organic solvent ratio is between about. 1:0.5 and about 1:2.

9. A reagent according to claim 1, wherein the sample is selected from the group consisting of biological fluids, industrial fluids, enviornmental fluids, and physiological fluids.

10. A reagent according to claim 7, wherein the sample is a biological fluid.

11. A reagent according to claim 9, wherein the sample is a physiological fluid.

12. A reagent according to claim 10, wherein the biological fluid is serum, plasma, urine, cerebrospinal fluid, saliva, milk, broth, culture media or supernatent.

13. A reagent according to claim 12, wherein said biological fluid is blood serum.

14. A reagent according to claim 12, wherein said biological fluid is plasma.

15. A reagent according to claim 1, wherein the sample contains potassium and interfering sodium cations, and the cation concentration being determined is the concentration of potassium cations, wherein the reagent consists essentially of a chromogenic cryptand 2.2.2, a non-chormogenic sodium mask, dioxane as the water-miscible organic solvent, cyclohexylaminopropane-sulfonic acid and tetramethylammonium as the buffer, and sorbitan monooleate as the surfactant.

16. A reagent for determining the concentration of sodium cations present in a sample containing sodium and interfering potassium cations, the reagent consisting essentially of:
(a) at least one chromogenic cryptand compound having the formula

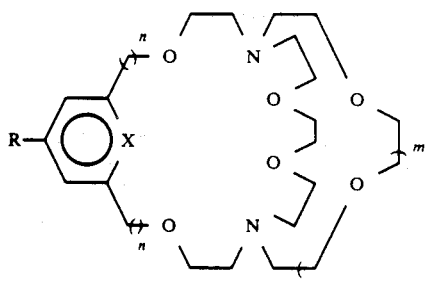

where n and m = 0 or 1, X = N or COH, and R = p-nitrophenylazo, 3-phenylisothiazolyl-5-azo, isothiazolyl-5-azo, thiazolyl-5-azo, 2,4,6-trinitrophenylazo, p-nitrostyryl, p-benzoquinonemonoimino, and bis-(p-dimethylaminophenyl)hydroxymethyl, and (b) at least one potassium mask which reacts selectively with the interfering potassium cations.

17. A reagent according to claim 16, wherein the mask is a spherand pre-organized for the ionic diameter of potassium.

18. A reagent according to claim 16, wherein the mask is a hemispherand pre-organized for the ionic diameter of potassium.

19. A reagent according to claim 16, wherein the mask is a cryptahemispherand pre-organized for the ionic diameter of potassium.

20. A reagent according to claim 16, wherein the mask is a cryptand having a cavity size about the size of a potassium ion.

21. A reagent according to claim 16, wherein the mask is a corand having a cavity size about the size of a potassium ion.

22. A reagent according to claim 16, wherein the sample contains sodium and interfering potasssium cations and the cation concentration being determined is the concentration of sodium cations, wherein the reagent consists essentially of a chromogenic cryptand 2.2.2, a non-chromogenic potassium mask, and cyclohexyl aminopropanesulfonic acid and tetramethylmmonium hydroxide as the buffer.

23. A method for determining the concentration of potassium cations present in a sample containing potassium and interfering sodium cations, comprising the steps of:
(a) preparing a reagent mixture consisting essentially of:
(i) at least one chromogenic cryptand compound having the formula

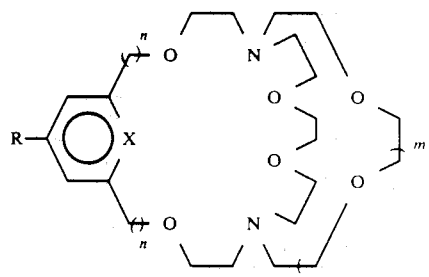

where n and m = 0 or 1, X = N or COH, and R = p-nitrophenylazo, 3-phenylisothiazolyl-5-azo, isothiazolyl-5-azo, thiazolyl-5-azo, 2,4,6-trinitrophenylazo, p-nitrostyryl, p-benzoquinonemonoimino, and bis-(p dimethylaminophenyl)hydroxymethyl, and bis-(p-dimethylaminophenyl)hydroxymethyl, and
(ii) at least one potassium mask which reacts selectively with the interfering potassium cations;
(b) combining said reagent with said sample;
(c) measuring the absorbance of the resulting solution; and
(d) comparing the absorbance so measured with the absorbance of standard compositions containing known concentrations of sodium cations.

24. A method according to claim 23, wherein the mask is a spherand pre-organized for the ionic diameter of sodium.

25. A method according to claim 23, wherein the mask is a hemispherand pre-organized for the ionic diameter of sodium.

26. A method according to claim 23, wherein the mask is a cryptahemispherand pre-organized for the ionic diameter of sodium.

27. A method according to claim 23, wherein the mask is a cryptand having a cavity size about the size of a sodium ion.

28. A method according to claim 23, wherein the mask is a corand having a cavity size about the size of a sodium ion.

29. A method according to claim 23, wherein said reagent of step (a) further comprises:
(iii) water;
(iv) a water-miscible organic solvent, and
(v) a buffer for maintaining said reagent pH at between about 9 and about 12.

30. A method according to claim 29, wherein said reagent further comprises;
(vi) a surfactant, and
(v) wherein the water to organic solvent ratio of said reagent is between about 1:0.5 and about 1:2.

31. A method according to claim 30, wherein the surfactant is selected from the group including polyoxyethylenelauryl ethers and sorbitan monooleate.

32. A method for determining the concentration of sodium cations present in a sample containing sodium and interfering potassium cations comprising the steps of:
(a) preparing a reagent mixture consisting essentially of:
(i) at least one chromogenic cryptand compound having the formula

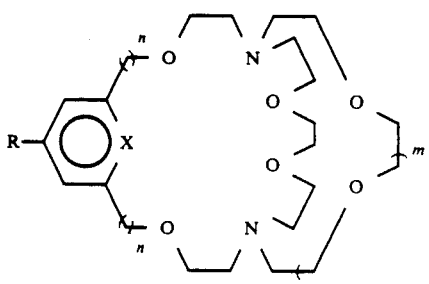

where n and m =0 or 1, X=N or COH, and R=p-nitrophenylazo, 3-phenylisothiazolyl-5-azo, isothiazolyl-5-azo, thiazolyl-5-azo, 2,4,6-trinitrophenylazo, p-nitrostyryl, p-benzoquinonemonoimino, (ii) at least one sodium mask which reacts selectively with the intefering sodium cations;

(b) combining said reagent with said sample;

(c) measuring the absorbance of the resulting solution; and (d) comparing the absorbance so measured with the absorbance of standard compositions containing known concentrations of potassium cations.

33. A method according to claim 32, wherein the mask is a spherand pre-organized for the ionic diameter of potassium.

34. A method according to claim 32, wherein the mask is a hemispherand pre-organized for the ionic diameter of potassium.

35. A method according to claim 32, wherein the mask is a cryptahemispherand pre-organized for the ionic diameter of potassium.

36. A method according to claim 32, wherein the mask is a cryptand having a cavity size about the size of a potassium ion.

37. A method according to claim 32, wherein the mask is a corand having a cavity size about the size of a potassium ion.

38. A method for determining the concentration of potassium cations present in a sample containing potassium and interfering sodium cations, comprising the steps of:

(a) preparing a reagent mixture consisting essentially of:

(i) a surfactant;

(ii) at least one chromogenic cryptand compound having the formula

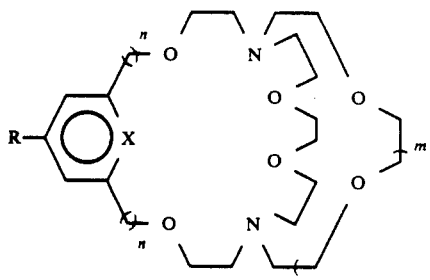

where n and m=0 or 1, X=N or COH, and R=p-nitrophenylazo, 3-phenylisothiazolyl-5-azo, isothiazolyl-5-azo, thiazolyl-5-azo, 2,4,6-trinitrophenylazo, p-nitrostyryl, p-benzoquinonemonoimino, and bis-(p-dimethylaminophenyl)hydroxymethyl, and (iii) a buffer, (iv) at least one sodium mask which reacts selectively with the interfering sodium cations, and (v) water;

(b) adding said reagent mixture to a carrier matrix device;

(c) evaporating the water of said reagent mixture;

(d) adding said sample to the device;

(e) measuring the reflections of said carrier matrix device; and (f) comparing the reflectance so measured with the reflectance of standard compositions containing known concentrations of the potassium cations.

39. A method according to claim 38, wherein the mask is a spherand pre-organized for the ionic diameter of sodium.

40. A method according to claim 38, wherein the mask is a hemispherand pre-organized for the ionic diameter of sodium.

41. A method according to claim 38, wherein the mask is a crytahemispherand pre-organized for the ionic diameter of sodium.

42. A method according to claim 38, wherein the mask is a cryptand having a cavity size about the size of a sodium ion.

43. A method according to claim 38, wherein the mask is a corand having a cavity size about the size of a sodium ion.

44. A method according to claim 38, wherein the reagent has a pH of between about 9 and about 12.

45. A method according to claim 38, wherein the matrix comprises one or more substances selected from the group consisting of high-density polyethylene, ultra-high molecular weight polyethylene, polypropylene, polyvinylidene fluoride, polytetrafluoroethylene, nylon, polyvinylchloride, polyesters, polysulfones, and blends thereof.

46. A method according to claim 38, wherein the matrix is a hydrophobic porous polymer sheet.

47. A method of claim 38, wherein the matrix is coated with a hydrophilic surfactant.

48. A method of claim 38, wherein the surfactant is selected from the group including of polyoxethylene octyl phenols, polyoxethylene nonyl phenols, and polyoxethylene lauryl ethers.

49. A method for determining the concentration of sodium cations present in a sample containing sodium and interfering potassium cations, comprising the steps of:

(a) preparing a reagent mixture consisting essentially of:

(i) a surfactant;

(ii) at least one chromogenic cryptand compound having the formula

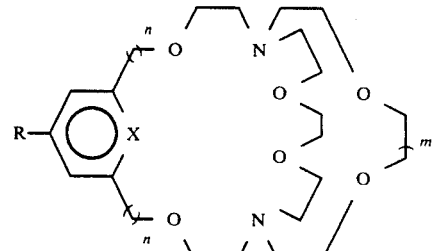

where n and m=0 or 1, X=N or COH, and R=p-nitrophenylazo, 3-phenylisothiazolyl-5-azo, isothiazolyl-5-azo, thiazolyl-5-azo, 2,4,6-trinitrophenylazo, p-nitrostyryl, p-benzoquinonemonoimino, and bis-(p-dimethylaminophenyl)hydroxymethyl, (iv) at least one potassium mask which reacts selectively with the intefering potassium cations, and (v) water;

(b) adding said reagent mixture to a carrier matrix device;

(c) evaporating the water of said reagent mixture;

(d) adding said sample to the device;

(e) measuring the reflectance of said carrier matrix device; and (f) comparing the reflectance so measured with the reflectance of standard compositions containing known concentrations of the sodium cations.

50. A method according to claim 49, wherein the mask is a spherand pre-organized for the ionic diameter of potassium.

51. A method according to claim 49, wherein the mask is a hemispherand pre-organized for the ionic diameter of potassium.

52. A method according to claim 48, wherein the mask is a cryptahemispherand pre-organized for the ionic diameter of potassium.

53. A method according to claim 49, wherein the mask is a cryptand having a cavity size about the size of a potassium ion.

54. A method according to claim 49, wherein the mask is a corand having a cavity size about the size of a potassium ion.

* * * * *